United States Patent
Joyce

(10) Patent No.: US 10,441,381 B2
(45) Date of Patent: Oct. 15, 2019

(54) MEDICAL ADHERENCE DEVICE

(71) Applicant: HEALTHBEACON, LTD., Dublin (IE)

(72) Inventor: James Joyce, Needham, MA (US)

(73) Assignee: HEALTHBEACON, LTD., Dublin (IE)

(*) Notice: Subject to any disclaimer, the term of this patent is extended or adjusted under 35 U.S.C. 154(b) by 330 days.

(21) Appl. No.: 14/307,002

(22) Filed: Jun. 17, 2014

(65) Prior Publication Data

US 2014/0374294 A1 Dec. 25, 2014

Related U.S. Application Data

(60) Provisional application No. 61/837,704, filed on Jun. 21, 2013, provisional application No. 61/916,899, filed on Dec. 17, 2013.

(51) Int. Cl.

| | |
|---|---|
| *G06K 7/01* | (2006.01) |
| *A61B 90/98* | (2016.01) |
| *G06F 19/00* | (2018.01) |
| *A61B 90/96* | (2016.01) |
| *A61B 50/36* | (2016.01) |
| *A61B 90/90* | (2016.01) |
| *A61B 90/00* | (2016.01) |

(52) U.S. Cl.
CPC .............. *A61B 90/98* (2016.02); *A61B 50/36* (2016.02); *A61B 50/362* (2016.02); *A61B 90/90* (2016.02); *A61B 90/96* (2016.02); *G06F 19/3456* (2013.01); *A61B 2090/0805* (2016.02); *G06F 19/3418* (2013.01)

(58) Field of Classification Search
CPC ..... A61B 19/0288; A61B 90/98; A61B 90/96; A61B 50/36; A61B 90/90; A61B 2090/0805; A61B 50/362; A61B 19/0287; G06F 19/3456; G06F 19/3418
See application file for complete search history.

(56) References Cited

U.S. PATENT DOCUMENTS

| | | | |
|---|---|---|---|
| 5,076,429 A | 12/1991 | Patrick et al. | |
| 5,259,501 A | 11/1993 | Withers et al. | |
| 9,168,104 B2* | 10/2015 | Dein | A61B 19/0256 |
| 9,326,742 B2* | 5/2016 | Hirschman | G16H 20/17 |
| 2005/0065640 A1* | 3/2005 | Mallett | B07C 7/005 |
| | | | 700/224 |

(Continued)

FOREIGN PATENT DOCUMENTS

| | | |
|---|---|---|
| GB | 2369109 A | 5/2002 |
| WO | 20070132237 A1 | 11/2007 |

OTHER PUBLICATIONS

Extended European Search Report for EP14814232.6; dated Jan. 16, 2017; 6 pages.

(Continued)

*Primary Examiner* — An T Nguyen
(74) *Attorney, Agent, or Firm* — Adler Pollock & Sheehan P.C

(57) ABSTRACT

Methods and apparatus for a medical adherence device. A medical adherence device includes a sharps bin, and an enclosure, the enclosure configured to display information on an output screen, receive medical waste and record information about the medical waste as the medical waste drops into the sharps bin.

7 Claims, 2 Drawing Sheets

(56) References Cited

U.S. PATENT DOCUMENTS

| | | | | |
|---|---|---|---|---|
| 2007/0080223 A1* | 4/2007 | Japuntich | G01K 1/024 | |
| | | | | 235/439 |
| 2007/0191690 A1* | 8/2007 | Hasse | A61M 5/14546 | |
| | | | | 600/300 |
| 2008/0139866 A1* | 6/2008 | Fisher | A61B 90/98 | |
| | | | | 588/249 |
| 2008/0184719 A1* | 8/2008 | Lowenstein | F25D 29/00 | |
| | | | | 62/127 |
| 2008/0190953 A1* | 8/2008 | Mallett | A61L 11/00 | |
| | | | | 221/13 |
| 2009/0317002 A1* | 12/2009 | Dein | A61B 19/0256 | |
| | | | | 382/224 |
| 2011/0036738 A1* | 2/2011 | Hiltl | B65F 1/0046 | |
| | | | | 206/459.1 |
| 2011/0163854 A1* | 7/2011 | Hamelin | A61B 90/96 | |
| | | | | 340/10.1 |
| 2011/0259471 A1* | 10/2011 | Maness | B09B 3/0075 | |
| | | | | 141/69 |
| 2011/0297567 A1* | 12/2011 | Maness | A61M 5/3205 | |
| | | | | 206/366 |
| 2011/0304315 A1 | 12/2011 | McElhinny et al. | | |
| 2012/0168443 A1* | 7/2012 | Maness | B09B 3/0075 | |
| | | | | 220/315 |
| 2012/0305132 A1* | 12/2012 | Maness | B09B 3/0075 | |
| | | | | 141/69 |
| 2013/0000530 A1 | 1/2013 | Coressel et al. | | |
| 2014/0374294 A1* | 12/2014 | Joyce | G06F 19/3456 | |
| | | | | 206/363 |
| 2015/0371199 A1* | 12/2015 | Ezell | G06Q 30/01 | |
| | | | | 705/303 |

OTHER PUBLICATIONS

International Search Report and Written Opinion received in International Application No. PCT/US2014/42733 dated Oct. 29, 2014, 7 pages.

* cited by examiner

MEDICAL ADHERENCE DEVICE

CROSS-REFERENCE TO RELATED APPLICATIONS

This application claims the benefit of U.S. Provisional Application No. 61/837,704, filed Jun. 21, 2013, and U.S. Provisional Application No. 61/916,899, filed Dec. 17, 2013, each of which is incorporated herein by reference.

BACKGROUND OF THE INVENTION

The present invention relates generally to sharps bins, and more particularly to a medical adherence device.

Traditional medical waste in the form of a needle and/or a syringe requires safe and regulated disposal in most jurisdictions. When patients are sent home with needles and/or syringes to self-administer medication they are often provided with a medical waste bin, sometimes referred to as a sharps bin. In general, a sharp is any device having corners, edges, or projections capable of cutting or piercing the skin, such as a needle of syringe. After each injection, a patient typically disposes of a needle and/or a syringe in the sharps bin. Each sharps bin is usually tracked by sharps bin delivery date, sharps bin collected date, and the date incinerated by a regulated medical waste disposal process service provider.

Ensuring that patients at home take their self-injected medication is a challenge for healthcare providers and pharmaceutical companies who often track how many sharps bins have been collected as a proxy for whether medication has been taken by a patient at home. In general, when a sharps bin is collected from a home location (or any location) it is sealed prior to collection, making it impossible to determine the number of syringes and/or needles in the sharps bin and or whether other waste has also been deposited into the sharps bin. Since it is unsafe and against health and safety practices, policies, and regulations the bin cannot be re-opened and the entire bin is typically incinerated.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides methods and apparatus for a medical adherence device.

In general, in one aspect, the invention features a medical adherence docking system including a sharps bin, and a docking station, the docking station comprising a base section support a lateral section, the lateral section supporting an arm section, the base section configured to receive and securely support a bottom portion of the sharps bin, and the arm section including a channel leading from an upper portion to a lower portion having a sensor located in the channel between the upper and lower portion, the channel adapted to receive a medical waste product and record information about the medical waste product using the sensor before the medical waste product exits the lower portion and into the sharps bin.

In another aspect, the invention features a medical adherence device including a sharps bin, and an enclosure, the enclosure configured to display information on an output screen, receive medical waste and record information about the medical waste before the medical waste drops into the sharps bin.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

Figure 1:
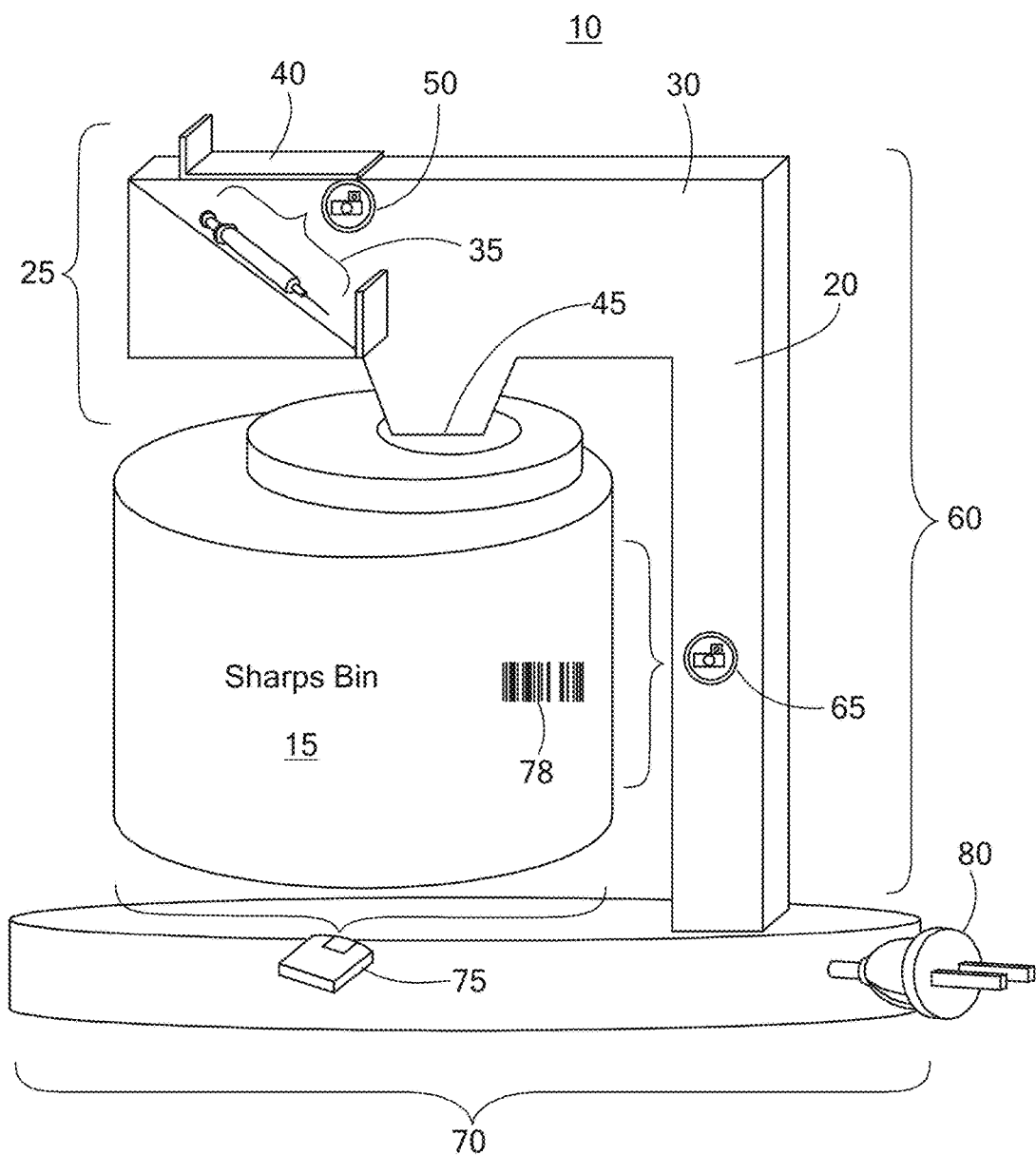
FIG. 1 is a block diagram of an exemplary medical adherence docking system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A, X employs B, or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As shown in FIG. 1 (original), in a first embodiment, an exemplary medical adherence docking system 10 includes a sharps bin 15 and a docking station 20. The sharps bin 15 and docking station 20 can be fabricated from metal, plastic or combinations thereof. The docking station 20 is configured to position the sharps bin 15 within and to capture and report patient adherence data. As used herein, patient adherence data includes, but is not limited to, a time and date in which a medical syringe is deposited in the sharps bin 15 through the docking station 20, and so forth. In implementations, patient adherence data may include a photographic image of an item deposited through the docking station 20 into the sharps bin 15.

More specifically, one implementation of the medical adherence docking system includes the docking station 20. A top section 25 includes an arm 30 containing a receptacle or channel 35 to receive, for example, a syringe. The receptacle 35 includes a top opening 40 and a bottom opening 45. Between the top opening 40 and the bottom opening 45 the receptacle 35 includes a sensor 50 that records a date and time of anything passing through the channel 35, e.g., a syringe. In one specific implementation, the receptacle 35 includes a photographic capture unit that captures a digital image of anything passing through the channel 35. In some implementations, the sensor 50 is configured to detect a weight of a syringe within the channel 35 before the syringe is released into the sharps bin 15. In another implementation, the sensor 50 is linked to a communications device (not shown), such as an Ethernet line or WiFi device, to enable transmission of data captured by the sensor 50 to be transmitted to another computing device.

Date, times, and optionally, digital images, are saved as data by the sensor 50 and may be read electronically using any one of various technologies, including, but not limited to, Radio-frequency identification (RFID), Near field communication (NFC), Bluetooth, and so forth.

In general, RFID is the wireless non-contact use of radio-frequency electromagnetic fields to transfer data, for the purposes of automatically identifying and tracking tags attached to objects. The tags contain electronically stored information.

In general, NFC is a set of standards for smartphones and similar devices to establish radio communication with each other by touching them together or bringing them into close proximity, usually no more than a few centimeters. NFC standards cover communications protocols and data exchange formats, and are based on existing radio-frequency identification (RFID) standards.

In general, Bluetooth is a wireless technology standard for exchanging data over short distances from fixed and mobile devices, creating personal area networks (PANs) with high levels of security.

The bottom opening 45 of the receptacle 35 mates with an opening 55 in the sharps bin 15. In one implementation, the bottom opening 55 includes a sliding door that releases a syringe into a safety funnel and through the opening 55 in the sharps bin 15.

The top section 25 is attached to, or an integral part of, a lateral section 60 of the docking station 20 supports the top section 25 and may include a device 65 such as a bar code reader, QR code reader, RFID reader, NFC reader, and so forth. A complimentary bar code, QR code, RFIF tag, or NFC card may be positioned on the outside of the sharps bin 15 at a location 78 proximate to the bar code reader, RFID reader, or NFC card located within the lateral section 60. In such a configuration, the lateral section 60 of the docking station 20 can identify the sharps bin 15. The identification can include reading a serial number of the sharps bin 15. In one implementation, the identification is sent to and stored by the sensor 50 in the channel 35.

In another a specific implementation the top section 25 of docking station 20 is detachable and becomes a cap that fastens to the top of the sharps bin 15 and is able to perform the function of safely depositing the needle, time stamping and photographing the needle before depositing it into the sharps bin 15.

The lateral section 60 is attached to, or an integral part of, a base section 70. The base section 70 is configured to provide a secure cradle for a bottom of the sharps bin 15. In one implementation, the base section 70 includes a weight measuring device 75, such as a scale. The scale 75 can be calibrated to a fully loaded weight of the sharps bin 15. When weight measuring device 75 detects that the weight of the sharps bin 15 is at certain value, the weight measuring device 75 may signal that the sharps bin 15 is full. Signaling can include flashing an indicator light. In one specific implementation, when the weight measuring device 75 detects the sharps bin is full, a date and/or time is sent to and stored by the sensor 50 in the channel 35.

Elements of the docking station 20 may be powered by a power supply 80 contained in the base section 70 (or other suitable location within the docking station 20). The power supply may be AC, DC or battery.

In a specific embodiment, the sharps bin 15 includes a Global Positioning System (GPS) device to enable remote monitoring of its location. In another specific implementation, the docket station 15 includes a GPS device to enable remote monitoring of its location.

In operation, each piece of medical waste, e.g., syringe, is loaded into the docking station 20 and then deposited into the sharps bin 15 after data has been collected. When the medical waste is deposited into the docking station 20, the medical waste is logged, photographed, weighed, time stamped and then safely deposited into the sharps bin 15. The docking station 20 captures this data at the time the syringe is being deposited into the docking station 20 and stores the event locally within docking station 20 and/or immediately transmits the data to a cloud-based (Web) application through an Internet connection which can include WIFI, broadband or other networks. The Web application may be used to determine what was deposited into the sharps bin 15 by optically matching the photograph against its database of medical needles and syringes. The docking station 20 reads the barcode and other identifiers on the sharps bin 15 and matches that against the specific waste that has been deposited. Reports may be generated for the data collected by the docking station 20.

Figure 2:
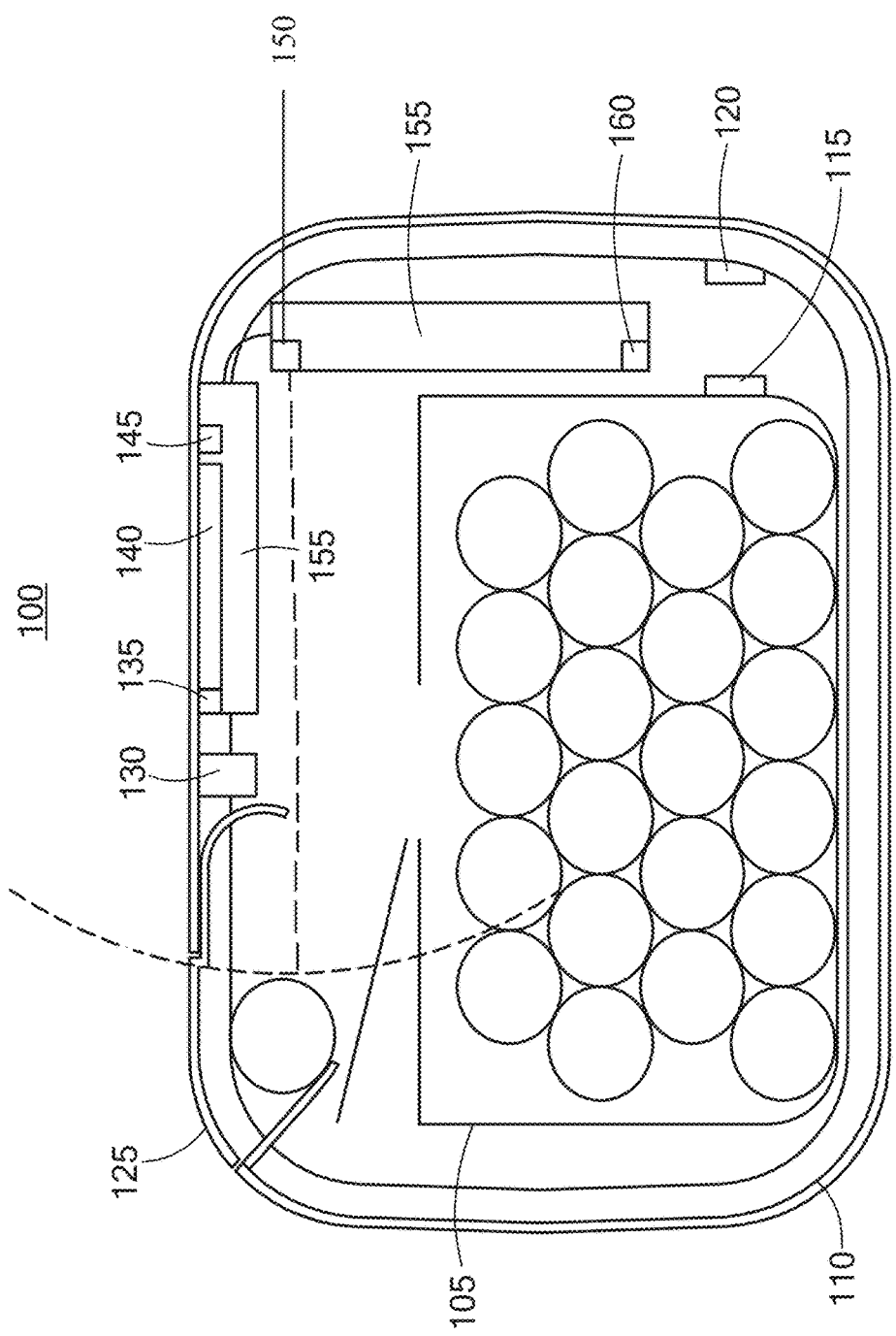
FIG. 2 is a block diagram of an exemplary medical adherence device.

As shown in FIG. 2, in a second embodiment, an exemplary medical adherence device 100 includes a sharps bin 105 positioned in an enclosure 110. The sharps bin 105 includes an identification device 115 such as a Bluetooth device, GPS device, near field communications card (NFC), bar code, QR code, RFID tag or other device. The sharps bin identification device 115 includes data specific to the sharps bin 105, such as an identification number or patient ID. In one embodiment, sharps bin identification device 115 is paired with an enclosure identification device 120 positioned in the enclosure 110. The enclosure identification device 120 can include, for example, a Bluetooth device, GOS device, NFC card reader, bar code reader, QR code reader, a RFID reader, and so forth.

In one embodiment, the sharps bin 105 is adapted to receive spent medical syringes. In other embodiments, the sharps bin 105 is adapted to other types of medical waste, such as spent medicine bottles, tubes, containers, and so forth. The enclosure 110 includes at least a hinged door 125 controlled by a release latch 130. The enclosure 110 also can include one or more of a sensor 135, a display screen 140, such as a liquid crystal (LCD) display, a power indicator 145, such as a light emitting diode (LED) light, a camera 150, and one or more sim cards 155 for wireless communication (e.g., exchange of data) to one or more cloud-based medical adherence applications.

In some embodiments, the enclosure 110 includes a universal serial bus (USB) 160 connector.

The display screen 140 is adapted to present data including, but not limited to, a status of the device 100 (e.g., full), a date, a position on a body of the patient where the patient should inject the medication, an adherence rating, and so forth.

In one embodiment, the release latch 130 opens the door 125 and activates the camera 150. In one embodiment, the door 125 includes a glass section that acts as a chamber for the syringe as an image is taken. In addition, the glass section may act as a safety mechanism so that a patient's hands are kept safe once a syringe is placed through the door 125. In still another embodiment, pressing on the door 125 activates the camera 150. The camera 150 remains activated until the door 125 closes, either manually or automatically. The camera 150 can include a sensor that stays active until a syringe passes through its field of view. Once the camera 150 detects a change in light representing the passage of the syringe through its field of view, or, in one specific implementation, the passing of the syringe through an infrared beam, an image is captured and stored, along with at least a time stamp. As soon as the image is captured, the camera 150 sends a signal to the door 125 to close. In addition, once the image is captured, information displayed on display device 140 is updated, reflecting real time patient habits. In one embodiment, the updated data includes an adherence score. The captured image and time stamp may be stored for further analysis and/or wirelessly transmitted by the one or more sim cards 155 to one or more cloud-based medical adherence applications.

The cloud-based medical adherence applications are adapted to analyze, summarize, and/or profile the received data for patient behaviors, possible medical interventions, and so forth. In addition, reports generated by the medical adherence applications may be used to support clinician and patient dialogue around adherence. In embodiments, the medical adherence applications present patient and clinician dashboards specifically targeted at a patient, a doctor and/or a pharmacist.

In one particular embodiment, the camera 150 detects the specific type of needle or waste and records the needle's serial number (or other unique identifier).

Elements of the medical adherence device 100 may be powered by an internal power supply located within the enclosure 110 or elsewhere. The internal power supply may be AC, DC or battery.

In operation, the display 140 flashes on the medical adherence device 100 to notify the patient and optionally indicates a current compliance rating and site for the injection. Once the patient has administered they return the spent syringe to the medical adherence device 100 where they press on the door or door release latch. The sensor in the camera 150 identifies that the door 125 is opening and activates the camera 150. The spent syringe is dropped through the door 125 and the camera sensor identifies its presence. The camera 150 takes an image of the syringe. Pressure is applied to the door 125 and the syringe is released through the door's rotation, dropping it into the sharps bin 105. The closing of the door 125 results in the patient's compliance rating being updated and displayed, along with a date for the next scheduled injection. In an embodiment, the display 140 remains active for a period of time before turning off.

Once the medical adherence device 100 is full is may be taken to a collection station such as a local pharmacy. At the collection station, an employee, such as a pharmacist, removes the sharps bin 105 and places it in a master sharps bin container. The master sharps bin container is adapted to receive multiple sharps bins. The master sharps bin is equipped with a sensor, such as camera, bar code reader, RFID reader, QR code reader, Bluetooth for example. When a sharps bin is placed in the master sharps bin, the master sharps bin sensor reads data from the sharps bin identification device of the sharps bin. This information may then be transmitted to one or more waste collection companies to enable efficient collections and control of the medical waste from the collection station. Multiple master sharps bins may be stacked or sit on a shelving unit. This information can be used to support dispensing, regulatory tracking including medicine recalls and give confirmation that the used medical device has been utilized and disposed.

The present invention is not only a tool for the safe disposal of medical waste such as needles and syringes, but also acts as a tool to accurately capture critical patient behavior as to whether they are complying with their medical treatments.

For example, if a patient is required to self-inject a medication weekly, immediately after injecting the medication, the syringe or device is safely deposited into the medical adherence device as they currently do with sharps bins. The patient is not required to take any other additional action. When the patient has deposited the needle into the medical adherence device this information is stored locally within the medical adherence device and/or immediately transferred to a cloud based server that analyzes the data, authenticates the data, and presents it as meaningful information for the purposes of understanding patient behavior.

In one embodiment, the medical adherence device is adapted to communicate with the user.

More particularly, the medical adherence device can track use of the device, and communicate with the user using text or speech (e.g., using a text to speech engine). The communication to the user may be a reminder to utilize the device. The device may be adapted to learn from patient interactions (e.g., using artificial intelligence, machine learning and pattern recognition techniques) and generate reminders, re-enforcements, and so forth, such that the patient is encouraged to maintain a regular routine.

The medical adherence device can be used to reconcile the quantities of medication consumed or not consumer by the user, and adapted to contact a pharmacy or physician through messaging. In the case of the pharmacy, this messaging could support the re-order of medications and directly integrate into the pharmacy ordering system. Once such a message is received by the physician or pharmacy, the patient can be notified of concerns. In one adaptation, the medical adherence device may be configured to telephone or text a caregiver or next of kin to insure the patient is healthy.

In one embodiment, the medical adherence device is adapted to interact more fully with a user.

For example, the medical adherence device can include audio features, such as speakers for music and/or a microphone that the user can use to receive assistance of any kind, e.g., input questions and receive answers, request verbal communication from a pharmacist or medical personnel, general information about the user's disease, and so forth. In one specific implementation, software resident in the medical adherence device can be updated remotely to reflect changes based on the questions and answers, and/or updates pertaining to information about the user's disease.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It is emphasized that the Abstract of the Disclosure is provided to comply with 37 C.F.R. Section 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical adherence docking system comprises:
   a sharps bin; and
   a docking station, the docking station configured to position the sharps bin within and comprising a base section support a lateral section, the lateral section supporting an arm section, the base section configured to receive and securely support a bottom portion of the sharps bin; and
   the arm section including a channel leading from an upper portion to a lower portion having a sensor located in the channel between the upper and lower portion, the channel adapted to receive a medical waste product and record patient adherence information about the medical waste product using the sensor before the medical waste product exits the lower portion and into the sharps bin, the patient adherence information transmitted to a patient's cloud-based clinical record and to communicate with the patient.

2. The system of claim 1 wherein the communication to the patient includes a reminder to utilize the docking station.

3. The system of claim 1 wherein the patient adherence information is used to generate reminders and re-enforcements such that the patient is encouraged to maintain a regular routine.

4. The system of claim 1 wherein the base section comprises a weight determining device.

5. The system of claim 1 wherein the lateral section comprises a communication device selected from the group consisting of bar code reader, QR code reader, RFID reader, NFC reader, and Bluetooth pairing device.

6. The system of claim 1 wherein the lower portion of the channel comprises a sliding door.

7. The system of claim 3 wherein the patient adherence information further comprises images.

* * * * *